US00PP32880P2

(12) United States Plant Patent
Arts

(10) Patent No.: US PP32,880 P2
(45) Date of Patent: Mar. 9, 2021

(54) ***MANDEVILLA* PLANT NAMED 'MAN220901'**

(50) Latin Name: *Mandevilla sanderi*
Varietal Denomination: MAN220901

(71) Applicant: MBA B.V., De Kwakel (NL)

(72) Inventor: Niels Arts, Aalsmeer (NL)

(73) Assignee: MBA B.V., De Kwakel (NL)

( * ) Notice: Subject to any disclaimer, the term of this patent is extended or adjusted under 35 U.S.C. 154(b) by 0 days.

(21) Appl. No.: 16/873,590

(22) Filed: May 14, 2020

(51) Int. Cl.
*A01H 5/02* (2018.01)
*A01H 6/08* (2018.01)

(52) U.S. Cl.
USPC ..... Plt./232
CPC ..... *A01H 6/088* (2018.05)

(58) Field of Classification Search
USPC ..... Plt./232
CPC ..... A01H 6/088
See application file for complete search history.

(56) References Cited

FOREIGN PATENT DOCUMENTS

QZ PBR 20200181 4/2020

OTHER PUBLICATIONS

UPOV hit on a *Mandevilla* plant named, 'MAN220901', QZ PBR 20200181, published Apr. 15, 2020.*

* cited by examiner

*Primary Examiner* — Anne Marie Grunberg
(74) *Attorney, Agent, or Firm* — C. Anne Whealy

(57) ABSTRACT

A new and distinct cultivar of *Mandevilla* plant named 'MAN220901', characterized by its upright to outwardly spreading and vining plant habit; vigorous growth habit; freely branching habit; relatively small glossy green-colored leaves; early and freely flowering habit; and pink-colored flowers with yellow-colored throats.

2 Drawing Sheets

Figure 1:
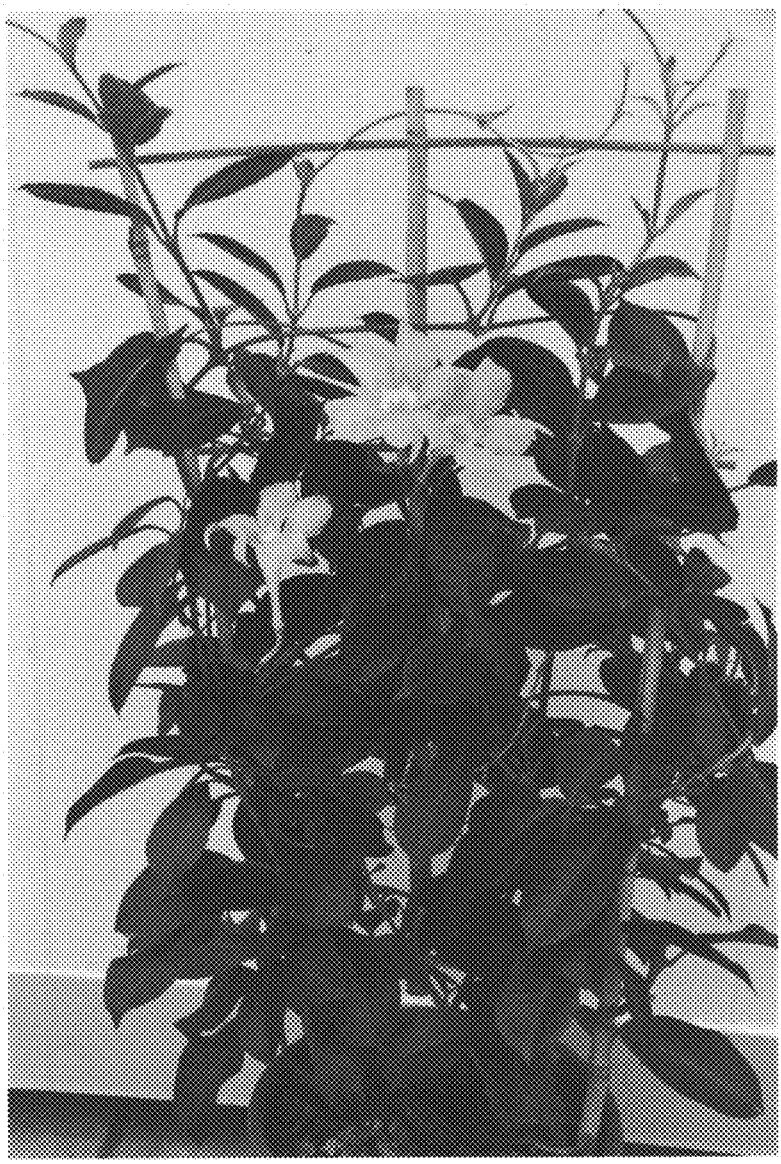

Botanical designation: *Mandevilla sanderi*.
Cultivar denomination: 'MAN220901'.

STATEMENT REGARDING PRIOR DISCLOSURES BY INVENTOR & APPLICANT

An European Community Plant Breeder's Rights application for the instant plant was filed by the Applicant, MBA B.V. of De Kwakel, The Netherlands, on Jan. 20, 2020, application number 2020/0181. Foreign priority is not claimed to this application.

The Inventor and Applicant assert that no publications nor advertisements relating to sales, offers for sale or public distribution occurred more than one year prior to the effective filing date of this application. Any information about the claimed plant would have been obtained from a direct or indirect disclosure from the Inventor or Applicant. Inventor and Applicant claim a prior art exemption under 35 U.S.C. 102(b)(1) for disclosure and/or sales prior to the filing date but less than one year prior to the effective filing date.

BACKGROUND OF THE INVENTION

The present invention relates to a new and distinct cultivar of *Mandevilla* plant, botanically known as *Mandevilla sanderi* and hereinafter referred to by the name 'MAN220901'.

The new *Mandevilla* plant is a product of a planned breeding program conducted by the Inventor in De Kwakel, The Netherlands. The objective of the breeding program is to create new freely-flowering *Mandevilla* plants with attractive flowers and good postproduction longevity.

The new *Mandevilla* plant originated from a cross-pollination in De Kwakel, The Netherlands in August, 2014 of a proprietary selection of *Mandevilla sanderi* identified as code number 12-0152-062, not patented, as the female, or seed parent with a proprietary selection of *Mandevilla sanderi* identified as code number 14-0016, not patented, as the male, or pollen, parent. The new *Mandevilla* plant was discovered and selected by the Inventor as a single flowering plant from within the progeny of the stated cross-pollination in a controlled greenhouse environment in De Kwakel, The Netherlands during the spring of 2017.

Asexual reproduction of the new *Mandevilla* plant by vegetative cuttings in a controlled greenhouse environment in De Kwakel, The Netherlands, since the summer of 2017 has shown that the unique features of this new *Mandevilla* plant are stable and reproduced true to type in successive generations.

SUMMARY OF THE INVENTION

Plants of the new *Mandevilla* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'MAN220901'. These characteristics in combination distinguish 'MAN220901' as a new and distinct *Mandevilla* plant:

1. Upright to outwardly spreading and vining plant habit.
2. Vigorous growth habit.

3. Freely branching habit.
4. Relatively small glossy green-colored leaves.
5. Early and freely flowering habit.
6. Pink-colored flowers with yellow-colored throats.

Plants of the new *Mandevilla* can be compared to plants of the female parent selection. Plants of the new *Mandevilla* differ primarily from plants of the female parent selection in flower color as plants of the new *Mandevilla* have pink-colored flowers with yellow-colored throats whereas plants of the female parent selection have white-colored flowers.

Plants of the new *Mandevilla* can be compared to plants of the male parent selection. Plants of the new *Mandevilla* differ primarily from plants of the male parent selection in flower color as plants of the new *Mandevilla* have pink-colored flowers with yellow-colored throats whereas plants of the male parent selection have white-colored flowers.

Plants of the new *Mandevilla* can be compared to plants of *Mandevilla hybrida* 'MAN216901', disclosed in U.S. Plant Pat. No. 29,001. In side-by-side comparisons, plants of the new *Mandevilla* differ primarily from plants 'MAN216901' in the following characteristics:

1. Plants of the new *Mandevilla* are more freely branching than plants of 'MAN216901'.
2. Leaves of plants of the new *Mandevilla* are slightly larger than leaves of plants of 'MAN216901'.
3. Plants of the new *Mandevilla* flower slightly later than plants of 'MAN216901'.
4. Plants of the new *Mandevilla* are not as freely flowering as plants of 'MAN216901'.
5. Plants of the new *Mandevilla* have pink-colored flowers with yellow-colored throats whereas plants of 'MAN216901' have bright white-colored flowers with light yellow-colored throats.

BRIEF DESCRIPTION OF THE PHOTOGRAPHS

The accompanying colored photographs illustrate the overall appearance of the new *Mandevilla* plant showing the colors as true as it is reasonably possible to obtain in colored reproductions of this type. Colors in the photographs may differ slightly from the color values cited in the detailed botanical description which accurately describe the actual colors of the new *Mandevilla* plant.

The photograph on the first sheet (FIG. 1 of 2) is a side perspective view of typical flowering plant of 'MAN220901' grown in a container.

Figure 2:
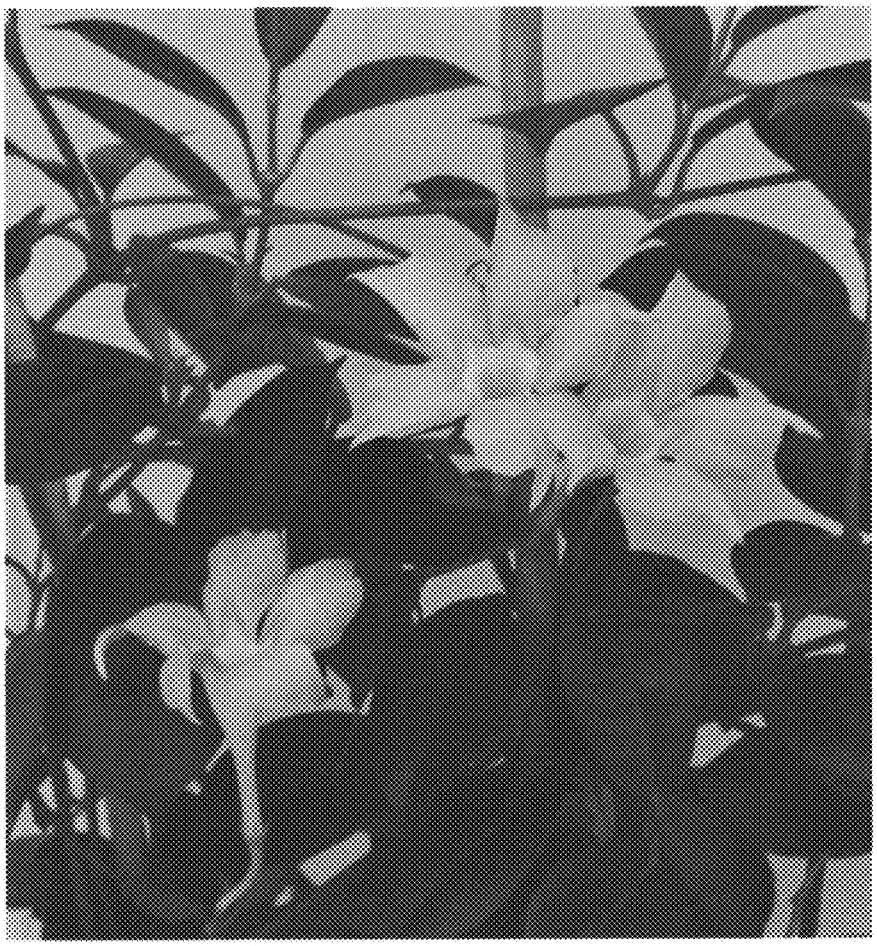

The photograph on the second sheet (FIG. 2 of 2) is close-up view of a typical flowering plant of 'MAN220901'.

DETAILED BOTANICAL DESCRIPTION

The aforementioned photographs and following observations, measurements and values describe plants grown during the autumn, winter and spring in 19-cm containers in a glass-covered greenhouse in De Kwakel, The Netherlands and under cultural practices typical of *Mandevilla* commercial production. During the production of the plants, day temperatures ranged from 20° C. to 22° C. and night temperatures averaged 18° C. Plants were pinched one time four weeks after planting and were ten months old when the photographs and description were taken. In the following description, color references are made to The Royal Horticultural Society Colour Chart, 1995 Edition, except where general terms of ordinary dictionary significance are used.

Botanical classification: *Mandevilla sanderi* 'MAN220901'.

Parentage:

*Female, or seed, parent*.—Proprietary selection of *Mandevilla sanderi* identified as code number 12-0152-062, not patented.

*Male, or pollen, parent*.—Proprietary selection of *Mandevilla sanderi* identified as code number 14-0016, not patented.

Propagation:

*Type*.—By vegetative cuttings.

*Time to initiate roots, summer*.—About 21 days at temperatures about 22° C.

*Time to initiate roots, winter*.—About 27 days at temperatures about 22° C.

*Time to produce a rooted young plant, summer*.—About 40 days at temperatures about 22° C.

*Time to produce a rooted young plant, winter*.—About 50 days at temperatures about 22° C.

*Root description*.—Medium in thickness, fibrous to slightly fleshy; typically whitish brown in color, actual color of the roots is dependent on substrate composition, water quality, fertilizers, substrate temperature and physiological age of roots.

*Rooting habit*.—Freely branching; dense.

Plant description:

*Plant and growth habit*.—Upright to spreading and vining plant habit; dense and bushy appearance; vigorous growth habit and moderate growth rate.

*Plant height, soil level to top of foliar plane*.—About 50 cm.

*Plant height, soil level to top of floral plane*.—About 60 cm.

*Plant diameter* (*spread*).—About 40 cm.

*Lateral branch description*.—Branching habit: Freely branching habit with about four primary branches, each with about three to five secondary lateral branches. Length, primary branches: About 25 cm to 35 cm. Diameter, primary branches: About 4 mm. Internode length: About 2 cm to 5 cm. Strength: Firm. Aspect: Upright to horizontal. Texture and luster: Smooth, glabrous; semi-glossy becoming woody and matte with development. Color, developing: Close to 143B. Color, developed: Close to 147C; when woody, close to 177D.

Leaf description:

*Arrangement*.—Opposite, simple; relatively small.

*Length, fully expanded leaves*.—About 7 cm to 8 cm.

*Width, fully expanded leaves*.—About 4 cm.

*Shape*.—Ovate.

*Apex*.—Acuminate.

*Base*.—Obtuse.

*Margin*.—Entire.

*Texture and luster, upper and lower surfaces*.—Smooth, glabrous; leathery; glossy.

*Venation pattern*.—Pinnate.

*Color*.—Developing leaves, upper surface: Close to 146A. Developing leaves, lower surface: Close to 146B. Full expanded leaves, upper surface: Close to 139A; venation, close to 143C. Fully expanded leaves, lower surface: Close to 146B; venation, close to 143D.

*Petioles*.—Length: About 1 cm to 1.5 cm. Diameter: About 2 mm. Strength: Strong. Texture and luster, upper and lower surfaces: Smooth, glabrous; semi-glossy. Color, upper and lower surfaces: Close to 143C.

Flower description:

*Flower type and flowering habit*.—Single salverform flowers arranged in axillary racemes; flowers star-shaped and face upright to outwardly; freely flowering habit with about eight to nine flowers per inflorescence and during the flowering season, about 115 flowers develop per plant.

*Natural flowering season*.—Plants flower continuously from late spring until the late summer in The Netherlands; early flowering habit, plants begin flowering about 7.5 months after planting.

*Flower longevity on the plant*.—About eight to ten days; flowers not persistent.

*Fragrance*.—None detected.

*Inflorescence height*.—About 13 cm.

*Inflorescence diameter*.—About 15 cm.

*Flower buds*.—Length: About 7 cm. Diameter: About 1.2 cm. Shape: Elongated, spindle-shaped. Texture and luster: Smooth, glabrous; semi-glossy. Color: Distally, close to 68B and proximally, close to 145B.

*Flowers*.—Appearance: Flared trumpet, corolla fused and five-parted. Diameter: About 8 cm to 9 cm. Length: About 4 cm to 6 cm. Throat diameter: About 1.5 cm. Tube length: About 4 cm to 5 cm. Tube diameter, proximally: About 4 mm.

*Corolla*.—Quantity and arrangement: Five petals arranged in a single whorl; proximal portion of the petals are fused into a tube; distal free portions somewhat imbricate. Petal length: About 4 cm. Petal width: About 2.5 cm to 3 cm. Petal shape and appearance: Ovate to triangular, asymmetrical. Petal apex: Acute. Petal margin: Entire; slightly undulate. Petal texture and luster, upper and lower surfaces: Smooth, glabrous; semi-glossy. Throat and tube texture: Smooth, glabrous; semi-glossy. Color: Petal, when opening and fully opened, upper surface: Close to 68B; towards the throat, close to 68A; venation, similar to lamina; color does not change with development. Petal, when opening and fully opened, lower surface: Close to 68B; towards the tube, close to 155D; venation, similar to lamina; color does not change with development. Throat: Distally, close to 155D and proximally, close to 12A; venation, similar to lamina. Tube: Distally, close to 155D and proximally, close to 14D; venation, similar to lamina.

*Calyx*.—Quantity and arrangement: Five sepals arranged in a single whorl; calyx, star-shaped. Length: About 5 mm to 8 mm. Diameter: About 6 mm. Sepal length: About 4 mm to 6 mm. Sepal width: About 2 mm. Sepal shape: Subulate. Sepal apex: Acute. Sepal margin: Entire. Sepal texture and luster, upper and lower surfaces: Smooth, glabrous; semi-glossy. Sepal color: When opening, upper and lower surfaces: Close to 145A. Fully opened, upper and lower surfaces: Close to 145A.

*Peduncles*.—Length: About 2 cm to 3 cm. Diameter: About 2 mm to 3 mm. Strength: Strong. Aspect: Mostly upright. Texture and luster: Smooth, glabrous; semi-glossy. Color: Close to 144A.

*Pedicels*.—Length: About 1.5 cm to 2 cm. Diameter: About 2 mm. Strength: Strong. Aspect: Upright to about 30° from peduncle axis. Texture and luster: Smooth, glabrous; semi-glossy. Color: Close to 144A.

*Reproductive organs*.—Stamens: Quantity and arrangement: Typically five; basifixed; anthers connivent. Filament color: Close to 12D. Anther length: About 6 mm to 8 mm. Anther shape: Elongate. Anther color: Close to 12D. Pollen amount: Moderate. Pollen color: Close to 12D. Pistils: Quantity: Typically one. Pistil length: About 1 cm to 1.5 cm. Style color: Close to 150B. Stigma diameter: About 2 mm. Stigma shape: Club-shaped. Stigma color: Close to 150D. Ovary color: Close to 144B.

*Fruits and seeds*.—To date, fruit and seed development have not been observed on plants of the new *Mandevilla*.

Pathogen & pest resistance: To date, plants of the new *Mandevilla* have not been noted to be resistant to pathogens and pests common to *Mandevilla* plants.

Temperature tolerance: Plants of the new *Mandevilla* have been observed to tolerate temperatures ranging from about 1° C. to about 45° C.

It is claimed:

1. A new and distinct *Mandevilla* plant named 'MAN220901' as illustrated and described.

* * * * *